United States Patent [19]

Morselli et al.

[11] 4,342,783

[45] Aug. 3, 1982

[54] ANTI-GLAUCOMA AGENT

[75] Inventors: Paolo L. Morselli, Meudon Bellevue, France; Louis De Santis, Jr.; Robert Adamski, both of Fort Worth, Tex.

[73] Assignee: Synthelabo, Paris, France

[21] Appl. No.: 164,223

[22] Filed: Jun. 30, 1980

[51] Int. Cl.³ .......................................... A61K 31/135
[52] U.S. Cl. .................................................. 424/330
[58] Field of Search ................... 424/330; 260/501.17, 260/501.19, 570.7

[56] References Cited

U.S. PATENT DOCUMENTS

| | | | |
|---|---|---|---|
| 3,674,840 | 7/1972 | Grandstrom et al. | 260/570.7 X |
| 3,712,890 | 1/1973 | Lee | 260/570.7 X |
| 3,723,476 | 3/1973 | Nakanishi et al. | 424/325 |
| 3,873,600 | 3/1975 | Brandstrom et al. | 260/570.7 X |
| 3,876,802 | 4/1975 | Brandstrom et al. | 424/330 |
| 3,888,898 | 6/1975 | Koppe et al. | 260/570.7 X |
| 3,937,834 | 2/1976 | Hunger et al. | 424/330 |
| 4,085,136 | 4/1978 | Tucker | 260/570.7 X |
| 4,145,442 | 3/1979 | Berntsson et al. | 424/330 |

FOREIGN PATENT DOCUMENTS

| | | | |
|---|---|---|---|
| 5662M | 1/1968 | France | 260/570.7 |
| 7015123 | 2/1971 | France | 260/570.7 |
| 7105224 | 2/1974 | France | 260/570.7 |

*Primary Examiner*—Douglas W. Robinson
*Attorney, Agent, or Firm*—Wegner & Bretschneider

[57] ABSTRACT

1-{4-[2-(Cyclopropylmethoxy)-ethyl]-phenoxy}-3-isopropylamino-propan-2-ol and its pharmaceutically acceptable salts, in the form of a racemate or optical isomer, are useful as topical anti-glaucoma agents.

3 Claims, No Drawings

ANTI-GLAUCOMA AGENT

A method of treating a patient having glaucoma is provided which comprises treating said patient with a compound of the formula:

or a pharmaceutically acceptable salt thereof, either as a racemate or optical isomer thereof. The compound is preferably administered in the form of eye drops applied in a solution containing 0.1% to 2.0% of the compound (I), with a representative example being 0.25%. The amount of the eye drops to be used will vary dependant upon the concentration. With 0.25% concentration being used, one drop per day may be used, or up to four drops per day.

The compound (I) of the present invention is prepared in accordance with the method of British Pat. No. 1,515,978 granted Oct. 18, 1978. The compound (I) is disclosed in Example III of U.S. Pat. No. 4,252,984, granted Feb. 24, 1981.

EXAMPLE I

1-{4-[2-(Cyclopropylmethoxy)-ethyl]-phenoxy}-3-isopropylamino-propan-2-ol and its hydrochloride

[(I); m=2; n=0; p=2; q=1; R=CH—(CH$_3$)$_2$; X=0; code number: SL-D.212]

Preparation of the starting compound 78.5 g (0.435 mol) of ethyl p-hydroxyphenylacetate, partially dissolved in 100 ml of ethanol, are introduced into a one liter 3-necked flask equipped with a mechanical stirrer, a dropping funnel, a reflux condenser and a thermometer and a solution of sodium ethylate (prepared from 100 ml of ethanol and 10.01 g of sodium), followed by 55 ml (0,4785 mol) of pure benzyl chloride are added dropwise. The mixture is kept at the reflux temperature of the solvent for 8 hours, the sodium chloride precipitated is then filtered off and the solution is evaporated to dryness. The residue is dissolved in ether and the ether solution is washed first with water, then with a N sodium hydroxide solution and again with water. It is dried over sodium sulphate, the ether is evaporated and the residue is rectified.

80.2 g (yield=68%) of ethyl p-benzoxy-phenylacetate boiling at 180°/0.07 mm Hg, are thus obtained.

200 ml of tetrahydrofurane are introduced into a 2 liter reactor equipped with a mechanical stirrer, a dropping funnel, a reflux condenser and a thermometer and are cooled before adding 6.6 g of lithium aluminium hydride under a nitrogen atmosphere. This suspension is cooled to −5° and 80 g (0.296 mol) of ethyl p-benzoxyacetate are added dropwise thereto in such a way that the temperature does not exceed 0°.

The whole is then kept at ambient temperature for 3 hours. The reaction mixture is then cooled and the excess AlLiH$_4$ is destroyed with an excess of sodium potassium double tartrate, the mixture is filtered and the residue is evaporated.

The 2-(p-benzoxyphenyl)-ethanol is caused to crystallise by trituration in isopropyl ether. 58.4 g (yield=86%) of this product are obtained; M.p.: 86°–88°.

2.6 g (0.055 mol) of sodium hydride are suspended in 20 ml of dimethylformamide in a 250 ml flask equipped with a magnetic stirrer, a dropping funnel and a reflux condenser. 11.4 g (0.05 mol) of 2-(p-benzoxyphenyl)-ethanol dissolved in 30 ml of the same solvent are then added. The mixture is gently heated to 30° and a further 70 ml of dimethylformamide are then added. A precipitate is observed. 7.42 g (0.055 mol) of cyclopropylmethyl bromide dissolved in 20 ml of dimethylformamide are then added and the mixture is heated for 8 hours to a temperature of 60°.

Progressive disappearance of the solid product is observed.

The reaction mixture is poured into water and extracted with ether, and the ether solution is washed with water, dried over sodium sulphate and evaporated to dryness. The solid residue is stirred for 30 minutes in petroleum ether; the insoluble 2-(p-benzoxyphenyl)-ethanol which has not reacted is then filtered off, the solvent is evaporated and the residue is rectified.

5.9 g (yield=74%) of 4-[2-(cyclopropyl-methoxy)-ethyl]-1-benzoxy-benzene are thus obtained. Boiling point=182°–184°/0.07 mm Hg.

The debenzylation of the preceding compound to 4-[2-cyclopropyl methoxy)-ethyl]-phenol is carried out under conditions similar to those described in Example I. The phenol is obtained in a yield of 84%. It boils at 138°/0.07 mm Hg.

(1) 1 g of sodium hydroxide pellets (0.025 mol) is added to a suspension of 3.8 g of the preceding compound in 30 ml of water. When the solution is homogeneous, 2.3 ml of epichlorohydrin are added and the mixture is stirred for 8 hours. It is then extracted with ether and the extract is washed with water, dried over sodium sulphate and evaporated to dryness.

The compound is purified by passing it over a silica column. 2.4 g of 1-{4-[2-(cyclopropylmethoxy)-ethyl]-phenoxy}-2,3-epoxy-propane are thus obtained (Rf=0.45;SiO$_2$; CHCl$_3$).

(2) 4.9 g of the preceding compound (0.02 mol) are condensed with 25 ml of isopropylamine by contact for 8 hours at ambient temperature and then by heating for 48 hours at the reflux temperature. After evaporation to dryness, the compound obtained is crystallised from petroleum ether.

5 g (yield=80%) of 2-{[4-(2-cyclopropyl-methoxy)-ethyl]-phenoxy}-3-isopropylamino-propan-2-ol are thus obtained. M.p.=70°–72° C.

Hydrochloride (SLD-212)

This is prepared by dissolving the base in the minimum amount of acetone and adding a solution of hydrochloric acid in ether until the pH is acid. The hydrochloride which has precipitated is filtered off and is recrystallised twice from acetone. M.p.=116° C.

| Analysis: | | | | |
|---|---|---|---|---|
| Calculated %: | C 62.86 | H 8.79 | N 4.07 | Cl 10.30 |

| -continued | | | | |
|---|---|---|---|---|
| | Analysis: | | | |
| Found %: | 62.48 | 8.79 | 4.07 | 10.50 |
| | 62.56 | 8.65 | 3.98 | 10.54 |

The NMR spectrum has confirmed the structure.

EXAMPLE II

Drops are made by dissolving sufficient quantity of compound of the Ex. I in distilled water to give 0.1%, 0.5%, 0.75%, and 2.0% solutions of the compound (I). Two drops are administered to the eye of normal and ocular induced hypertensive rabbits. The intraocular pressure of both the normal and ocular induced hypertensive rabbits was reduced significantly as measured at intervals over a 6-hour period.

We claim:

1. A method of treating glaucoma in a patient which comprises administering topically to the eye of said patient a compound of the formula:

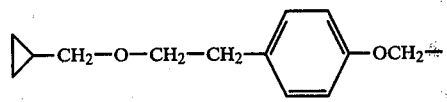

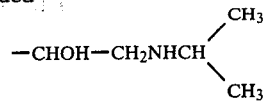

or a pharmaceutically acceptable salt thereof in the form of a racemate or optical isomer thereof in an amount effective to treat glaucoma by reducing interocular pressure.

2. An eye drop of claim 1 wherein said effective amount is from about 0.1 to about 2.0% of said eye drop.

3. An eye drop for the treatment of glaucoma through topical application of said eye drop to the eye of a patient suffering from glaucoma, comprising a therapeutically effective amount of a compound of the formula,

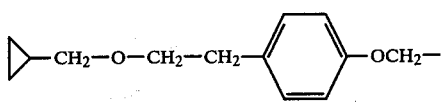

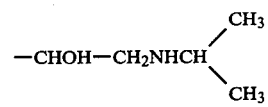

or a pharmaceutically acceptable salt thereof, said compound being a racemate or optical isomer, said amount being effective to treat glaucoma by reducing interocular pressure, and a solvent for said compound which is suitable for topical application to the eye of a patient.

* * * * *